United States Patent [19]

Morris

[11] 4,307,472

[45] Dec. 29, 1981

[54] PROSTHETIC DEVICE WITH RIGID IMPLANTABLE MEMBER HAVING BONDED POROUS COATING

[75] Inventor: Harold B. Morris, Newnan, Ga.

[73] Assignee: Glasrock Products, Inc., Fairburn, Ga.

[21] Appl. No.: 136,977

[22] Filed: Apr. 3, 1980

Related U.S. Application Data

[60] Division of Ser. No. 914,737, Jun. 12, 1978, Pat. No. 4,213,816, and a continuation-in-part of Ser. No. 764,952, Feb. 2, 1977, abandoned.

[51] Int. Cl.³ ............................. A61F 1/00; A61F 1/24
[52] U.S. Cl. ............................................... 3/1; 3/1.91; 3/1.913; 128/92 C
[58] Field of Search ................................... 3/1.9–1.913; 128/92 C, 92 CA

[56] References Cited

U.S. PATENT DOCUMENTS

| | | | |
|---|---|---|---|
| 3,879,767 | 4/1975 | Stubstad | 3/1.91 |
| 3,886,600 | 6/1975 | Kahn et al. | 3/1.91 |
| 3,938,198 | 2/1976 | Kahn et al. | 3/1.913 X |
| 3,986,212 | 10/1976 | Sauer | 3/1.91 |
| 4,007,494 | 2/1977 | Sauer | 3/1.9 |

*Primary Examiner*—Ronald L. Frinks
*Attorney, Agent, or Firm*—Lane, Aitken, Kice & Kananen

[57] ABSTRACT

A method for bonding a layer of porous polymeric material to a rigid implantable portion of a prosthetic device, which includes the steps of (a) forming a substrate by coating the implantable portion with material which is chemically compatible with the porous polymeric material and which has a melt viscosity and/or melting temperature lower than that of the porous polymeric material, (b) covering the substrate with a porous polymeric material in powder form capable of forming said porous polymeric layer for forming a composite coating on the implantable portion, and (c) heating the substrate and porous polymeric material to a temperature high enough to cause the substrate material to flow into the adjacent pores and low enough so that the porous material will maintain its shape so that the porous layer will be bonded to the substrate and the outer pores will be open to accommodate tissue ingrowth, and an apparatus formed by said method.

4 Claims, No Drawings

PROSTHETIC DEVICE WITH RIGID IMPLANTABLE MEMBER HAVING BONDED POROUS COATING

BACKGROUND OF THE INVENTION

This is a division, of application Ser. No. 914,737 filed June 12, 1978 now U.S. Pat. No. 4,213,816 and a continuation-in-part of copending U.S. patent application Ser. No. 764,952, filed Feb. 2, 1977, now abandoned.

This invention relates to a method for anchoring a thin layer of a porous polymeric material to the rigid structural component of a surgical implantation device and, more particularly, to a method which includes the step of forming a substrate of a material with a melt viscosity and/or melting temperature lower than that of the porous material between the structural component and the porous outer layer.

Surgical implantation devices which utilize tissue ingrowth to anchor the devices in place in the human body are being used more frequently. U.S. patent application Ser. No. 567,296, filed Apr. 11, 1975, and issued as U.S. Pat. No. 3,986,212, assigned to the same party as the instant invention is directed to the use of porous polymeric materials as a coating on the outer surface of structural components of joint prostheses where a spike or stem portion is inserted into the medullary canal and the teachings of that patent are hereby incorporated into this application by reference. As described in the above patent, the porous material is effective in accommodating and promoting tissue ingrowth throughout the entire porous layer, but strong enough when ingrowth occurs to withstand stresses to which the devices are subjected.

Such coatings have conventionally been formed by a physical connection between the porous layer and the underlying structural component. For example, the underlying unit has been modified by forming fenestrations, grooves, slots, undercut channels or other surface irregularities for holding the porous layer in place. It has been found, however, that the bond strength between the porous layer and the structural member is relatively low because there are large areas of contact with no adhesion and the area of the porous layer which is actually bonded to the structural member is small relative to the total contact surface. The provision of holes or grooves in the underlying structural member is not a satisfactory solution since they tend to weaken the prosthesis and compensation must be made in the design by strengthening the member. Another disadvantage of a coating which is not adhered to the prosthesis along the entire contact surface is that any exposed edges which are not directly adhered are susceptible to fracture, peel or breakage.

SUMMARY OF THE INVENTION

The problems discussed above are solved, in accordance with the invention, by providing an interfacial layer or substrate between the underlying structural component and the porous coating, which forms a bond between the porous layer along its entire contact surface and provides a remarkably greater "pull" or "peel" strength.

The underlying surface is roughened or otherwise prepared by providing grooves or other irregularities thereon. A knurled surface formed by a number of shallow grooves has been found to be preferable. It has been found that because of the significantly greater bond strength provided by the inventive process, the grooves need not be as deep as those used previously so that the underlying structural member is not weakened.

The substrate is chemically compatible with the material of the porous outer layer and is coated on the underlying structural member in a thin layer by a suitable technique such as, for example, dipping, brushing or flowing (e.g., where powder is sprinkled on and melted). For example, where porous polyethylene is used as the porous material, non-porous polyethylene can be used for the substrate.

The porous layer is formed on the outer surface of the substrate. The material used for the substrate has a melt viscosity and/or melting temperature lower than that of the porous material so that the interfacial connection between the substrate and porous layer is formed by heating the composite which causes the substrate to flow into the adjacent pores. Although the surface preparation of the underlying unit is significantly less severe than for prior art devices where the porous layer was applied directly to the underlying surface, the bond strength is substantially greater. This is believed to be caused by the fact that since the inter-medullary stem is almost entirely encapsulated, any separating force applied to the porous layer is distributed over the entire interfacial connection and not just to a small portion of the area mechanically attached to the underlying surface.

DETAILED DESCRIPTION OF A PREFERRED EMBODIMENT

It has been found that polyolefins of the type described in the aforementioned patent application are biocompatible, provide an excellent environment for tissue ingrowth and are able to withstand stress to which prosthetic devices are normally subjected.

For the porous outer layer polyolefins with a melt index (ASTM D1238) ranging from less than 1 to 5 have been found to work effectively.

The substrate must be formed of a material which is chemically compatible with the porous outer layer. For example, when porous polyethylene is used as the outer layer, a non-porous polyethylene substrate with a density of about 0.95 g./c.c. can be used. Further, as in the above example when the same specie of polyolefinic polymer is used for both the porous matrix and substrate the melt index of the substrate must be greater than that of the porous outer layer. For example, when a polyolefin with a melt index ranging from less than 1 to 5 is used to form the porous matrix, the substrate should be formed of a material which has a melt index ranging from 5–25. To better understand the relative properties of the matrix and substrate materials the term melt index can best be described as being inversely proportional to the melt viscosity of a material, e.g. a low melt index indicates a high viscosity. Thus, the matrix material should be more viscous than the substrate.

The substrate can also be formed of a different specie of polyolefinic polymer than that of the porous matrix. Since different species have different melting temperatures, in order for the inventive method to work when different species are used the melt temperature of the substrate should be lower than that of the porous matrix. For example, if polypropylene is used to form the porous matrix, polyethylene can be used to form the substrate since it melts at a noticeably lower temperature than polypropylene. The underlying structural member which can be formed of stainless steel or Vitallium may be provided with surface irregularities, which can be in the form of, for example, annular rings or shallow grooves which form a diamond-shaped pattern (e.g. knurled). Annular rings 3 mm. wide and 1 mm. deep have been found to provide good results.

The substrate is applied to the underlying structure in a thin uniform layer. The thickness can vary from about 0.5 mm. for a finger joint prosthesis to about 1 mm. for a larger hip joint prosthesis. The substrate can be applied, for example, by coating the structural member by any of the following known methods: (1) dipping the structural member, which has been heated to above the melting point of the substrate material, into a fluidized bed of powdered material, (2) electrostatic spraying where the structural member, which may or may not be heated, is electrically charged and powder is sprayed onto the member from a nozzle with the opposite charge, (3) dipping the structural member into a liquid substrate material, or (4) forming a mold for providing a space around the structural member and filling the mold with a suitable powder and externally applying energy by a dielectric means to a temperature above the melting point of the substrate material.

The porous layer can be applied, for example, by methods (1), (2) or (4) as described above for forming the substrate. The porous layer should be at least 1 mm. thick, preferably ranging from 2-4 mm. depending on the type of prosthesis to which the layer is being applied. The heat or energy which is applied should be to a temperature above the melting point of the substrate material but below the melting point of the porous matrix which has a higher melt temperature and/or melt viscosity. The metal underlying structure will operate to transfer heat to the substrate material causing the substrate to soften simultaneously with conversion of the powdered material into the porous matrix. The temperature is such, and can easily be determined by one with ordinary skill in the art, that the substrate material will soften and the porous matrix will maintain its shape so that the substrate material will easily flow into the adjacent pores and anchor the two layers together.

In this manner a bond is formed between the substrate and porous layer which is significantly greater than heretofore possible when the porous layer was applied directly to the underlying structure. The composite formed as described above provides a much stronger bond between the outer layer of porous material and the underlying structural member because the porous layer is bonded along its entire surface, instead of at small localized sections. Further, since the structural component is almost entirely encapsulated any separating force is applied over the entire contact surface.

It should be understood that those with ordinary skill in the art will be able to make modifications and improvements which fall within the scope of the above invention, all of which are contemplated as falling within the intended scope of the appended claims.

I claim:

1. A prosthetic device with a rigid implantable portion and a layer of porous polymeric nonfibrous material bonded to said implantable portion, comprising a substrate coated on the implantable portion and formed of material chemically compatible with and having a melt viscosity lower than that of the porous polymeric material, the layer of porous polymeric material in the form of a matrix being attached to the substrate by means of the substrate material penetrating adjacent pores of the matrix and maintaining the outer pores open to accommodate tissue ingrowth.

2. A prosthetic device with a rigid implantable portion and a layer of porous polymeric nonfibrous material bonded to said implantable portion, comprising a substrate coated on the implantable portion and formed of material chemically compatible with and having a melting temperature lower than that of the porous polymeric material, the layer of porous polymeric material in the form of a matrix being attached to the substrate by means of the substrate material penetrating adjacent pores of the matrix and maintaining the outer pores open to accommodate tissue ingrowth.

3. A prosthetic device with a rigid implantable portion and a layer of porous polymeric material bonded to said implantable portion, comprising a substrate coated on the implantable portion and formed of a material chemically compatible with having a melt viscosity lower than that of the porous polymeric material, the layer of porous polymeric material being formed from powdered polymeric material applied to the substrate and converted to a matrix and being attached to the substrate by means of the substrate material penetrating the adjacent pores of the matrix and maintaining the outer pores open to accommodate tissue ingrowth.

4. A prosthetic device with a rigid implantable portion and a layer of porous polymeric material bonded to said implantable portion, comprising a substrate coated on the implantable portion and formed of a material chemically compatible with and having a melting temperature lower than that of the porous polymeric material, the layer of porous polymeric material being formed from powdered polymeric material converted to a matrix and being attached to the substrate by means of a substrate material penetrating adjacent pores of the matrix and maintaining the outer pores open to accommodate tissue growth.

* * * * *